(12) United States Patent
Lee

(10) Patent No.: US 6,397,842 B1
(45) Date of Patent: *Jun. 4, 2002

(54) FLUID-TREATMENT DEVICES

(75) Inventor: Andrew James Lee, Kent (GB)

(73) Assignee: Smiths Group Public Limited Company, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/312,962

(22) Filed: May 17, 1999

(30) Foreign Application Priority Data

Jun. 9, 1998 (GB) .............................................. 9812309

(51) Int. Cl.[7] .......................... A61M 16/00; F23D 11/00; F23D 14/00
(52) U.S. Cl. ............................ 128/203.26; 128/201.13; 128/205.12; 128/205.27; 128/205.29; 128/911; 55/497; 55/521
(58) Field of Search ....................... 128/201.13, 202.27, 128/203.26, 204.18, 205.17, 205.27, 205.29, 207.14, 911, 912; 55/497, 498, 421, 521; 210/321.77, 321.86, 446, 456, 493.1, 495.3, 493.5

(56) References Cited

U.S. PATENT DOCUMENTS

| | | | | |
|---|---|---|---|---|
| 2,058,669 A | * | 10/1936 | Dollinger ..................... 55/497 |
| 2,648,272 A | * | 8/1953 | Norton ......................... 55/521 |
| 2,912,982 A | * | 11/1959 | Barsky .................. 128/202.27 |
| 3,388,705 A | * | 6/1968 | Grosshandler ......... 128/202.27 |
| 3,713,440 A | * | 1/1973 | Nicholes ................. 128/201.13 |
| 3,873,288 A | * | 3/1975 | Wachter et al. ............... 55/497 |
| 3,912,795 A | * | 10/1975 | Jackson .................... 261/36 R |
| 4,297,117 A | * | 10/1981 | Holter et al. .................. 55/389 |
| 4,516,573 A | * | 5/1985 | Gedeon ................. 128/201.13 |
| 4,610,706 A | * | 9/1986 | Nesher ........................ 55/497 |
| 4,617,122 A | * | 10/1986 | Kruse et al. ............. 210/493.3 |
| 4,783,258 A | * | 11/1988 | Willinger et al. ........... 210/169 |
| 5,035,236 A | * | 7/1991 | Kanegankar ........... 128/201.13 |
| 5,053,125 A | * | 10/1991 | Willinger et al. ........... 210/169 |
| 5,284,160 A | * | 2/1994 | Dryden .................. 128/203.12 |
| 5,320,096 A | * | 6/1994 | Hans ...................... 128/205.29 |
| 5,546,930 A | * | 8/1996 | Wikefeldt .............. 128/201.13 |
| 5,674,302 A | * | 10/1997 | Nakayama et al. ........ 55/385.3 |
| 5,885,455 A | * | 3/1999 | Graus et al. ................ 210/445 |

FOREIGN PATENT DOCUMENTS

| | | |
|---|---|---|
| DE | 2216010 | 10/1973 |
| JP | 8-28376 | 1/1996 |

* cited by examiner

Primary Examiner—John G. Weiss
Assistant Examiner—Joseph F Weiss, Jr.
(74) Attorney, Agent, or Firm—Connolly Bove Lodge & Hutz, LLP

(57) ABSTRACT

A catheter mount incorporates a filter pleated along its length in zig-zag fashion. Opposite edges of the filter are sealed between identical upper and lower parts of a housing between teeth extending along opposite sides.

14 Claims, 3 Drawing Sheets

FLUID-TREATMENT DEVICES

BACKGROUND OF THE INVENTION

This invention relates to fluid-treatment devices.

The invention is more particularly concerned with medical devices for filtering, humidifying or otherwise treating fluid, such as air, flowing to or from a patient.

In one particular application of medical respiration systems, a filter or HME device is connected at the machine end of a tracheal tube and connection to the device is made by a so-called catheter mount, that is, a relatively large bore, corrugated, flexible tube. The catheter mount provides a flexible interconnection between the tracheal tube and ventilator tubing connected at the other end of the catheter mount. One problem, with filters in particular, is that high efficiency filters tend to have a high resistance to flow unless they have a large surface area, in which case they tend to be bulky and heavy. It is also a disadvantage to have several different components interconnected in a breathing circuit because it makes rapid assembly more difficult, it increases the deadspace within the circuit and it increases the risk of accidental detachment of components. Proposals have been made to overcome some of the problems of previous arrangements, as described in GB2321604 and GB2169522. Previously proposed arrangements, however, suffer from various problems, such as difficulties in making the filter element or of sealing it in a housing.

BRIEF SUMMARY OF THE INVENTION

It is an object of the present invention to provide an improved fluid-treatment device.

According to one aspect of the present invention there is provided a fluid-treatment device comprising a housing and a fluid-treatment element located in the housing to treat fluid flowing through the housing, the housing having an inlet and outlet port and being of elongate shape divided along its length into two parts, each part having a set of triangular tooth formations extending along opposite sides that mate with one another, the fluid-treatment element being pleated across its width in a zigzag fashion with the sides of the fluid-treatment element following the profile of the teeth formations on the housing, and opposite edges of the fluid-treatment element being supported and sealed between the teeth formation of the two parts of the housing such that fluid flowing between the two ports is confined to flow through the fluid-treatment element.

The housing is preferably flexible and corrugated. The two parts of the housing may be substantially identical. The fluid-treatment element is preferably a gas-treatment element such as an HME element or a filter. One of the parts of the housing preferably has a patient end fitting for connection to a tracheal tube connector, the other of the parts having a machine end fitting for connection to a ventilation tube connector. The two parts of the housing may be sealed with the fluid-treatment element by means of an adhesive or solvent along opposite edges of the fluid-treatment element. The fluid-treatment element may be supported by a ladder-shape support frame. The support frame may be of a thermoplastic material and the two parts of the housing may be sealed with the fluid-treatment element by causing material of the support frame to flow into sealing contact with both the fluid-treatment element and the two parts of the housing.

According to another aspect of the present invention there is provided an assembly including a fluid-treatment device according to the above one aspect of the invention, a tracheal tube, a connector connected between the tracheal tube and one end of the fluidtreatment device, ventilation tubing, and a connector connected between the ventilation tubing and the other end of the fluid-treatment device.

A catheter mount incorporating a filter, according to the present invention, will now be described, by way of example, with reference to the accompanying drawings.

DETAILED DESCRIPTION OF THE PREFERRED EMBODIMENT

Figure 1:
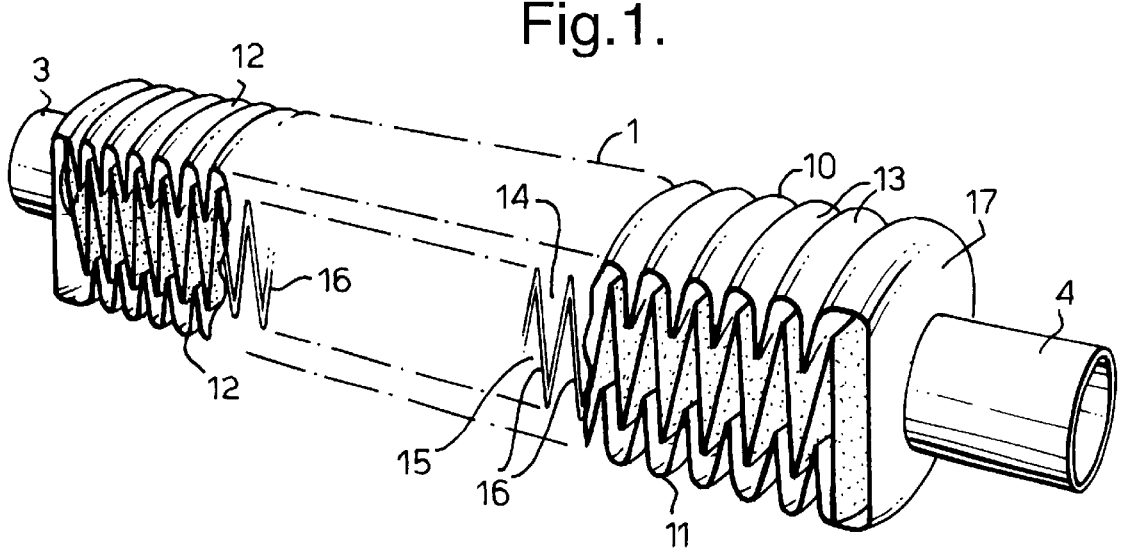
FIG. 1 is a perspective view of the catheter mount.

The catheter mount comprises a housing 1 containing a fluid-treatment element in the form of a filter 2 and having a patient end fitting 3 at one end and a machine end fitting 4 at the opposite end. In use, the patient end fitting 3 is connected to a standard connector in the machine end of a tracheal tube and the machine end fitting 4 is connected to a standard connector, such as a Y-piece connector at the end of ventilation tubing extending to ventilation equipment. Gas flows along the catheter mount alternately in opposite directions during the inspiration and exhalation phases respectively, and flows through the thickness of the filter element 2.

The housing 1 is moulded in two, identical parts 10 and 11 of a flexible plastics material, such as PVC, although these parts could be of different shapes, such as if one were to include a carbon dioxide sampling port. The two parts 10 and 11 form the upper and lower halves of the housing 1, which is essentially divided in half along its length with each part including a respective one of the end fittings 3 or 4. Each part 10 and 11 includes a rounded, convex upper or lower wall 12, which is formed with lateral corrugations 13 so as to make it more flexible in a plane normal to the wall. Each part 10 and 11 also includes a side wall 14 and 15 extending longitudinally on each side. Each side wall 14 and 15 is corrugated slightly on the outer surface of the housing to improve flexibility and is profiled along its edge with a series of triangular teeth 16. The teeth 16 on the two parts 10 and 11 are shaped to engage with one another. The end of the part 10 and 11 with the end fitting 3 or 4 is formed with a radially-extending flange 17, the opposite end 18 of the part being shaped to mate with the flange on the other part.

Figure 5:
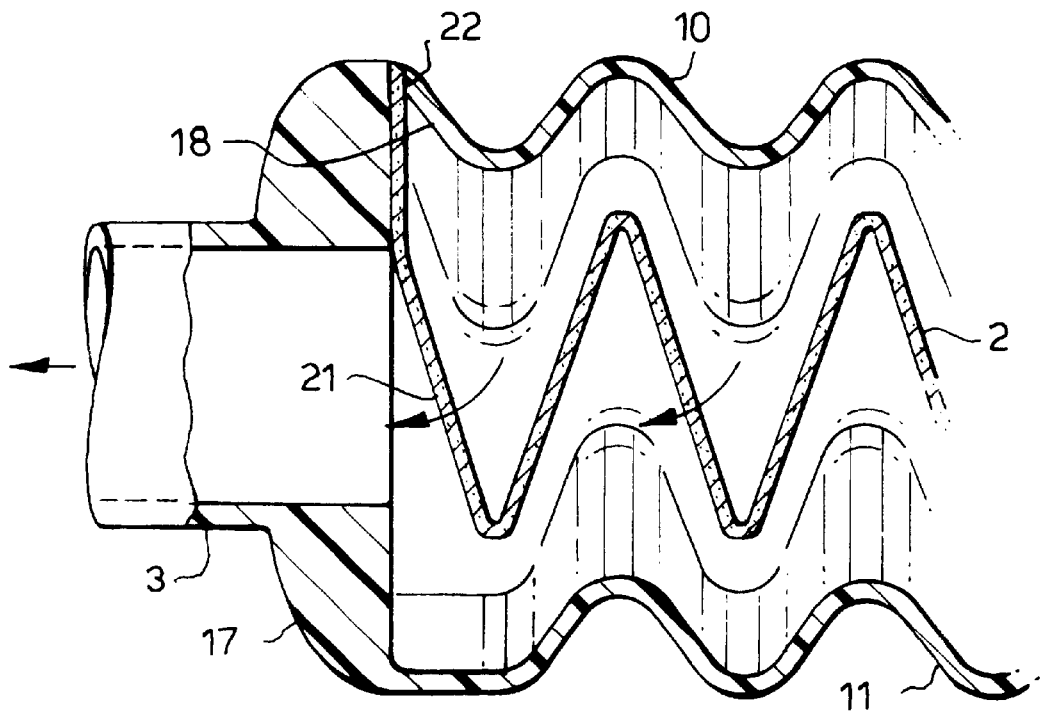
FIG. 5 is a cross-sectional side elevation view of one end of the mount.

The filter element 2 may be of any conventional filter material, such as a HEPA bacterial/viral filter of the kind used in the HEPA filter sold by SIMS Portex Limited of Hythe, Kent, England. The filter element 2 comprises a rectangular strip of material folded backwards and forwards in a zigzag fashion across its width into a number of inclined pleats 20 of V-shape, equal to the number of teeth 16 on the housing 1 and having a length equal to that of the sides of the teeth. The width of the filter element 2 is equal to that of the housing 1 so that the pleated element can be located with its opposite edges 21 supported on the teeth 16 along opposite sides of the housing. The edges 21 of the filter element 2 are sandwiched between the teeth 16 on the two parts 10 and 11 of the housing, with the lateral edges 22 of the pleats 20 at opposite ends (FIG. 5) being sandwiched between the flange 17 of one part of the housing and the opposite end 18 of the other part. Both longitudinal edges 21 and lateral edges 22 are sealed in a gas-tight fashion between the two parts 10 and 11 of the housing 1. This may be done in various ways. For example, a bead of an adhesive or solvent may be applied along the two parts 10 and 11 of housing 1 where they contact the filter element 2. Alternatively, heat may be used to cause material of the housing 1 or of the filter element 2 to flow forming a seal with the contacting component.

Figure 2:
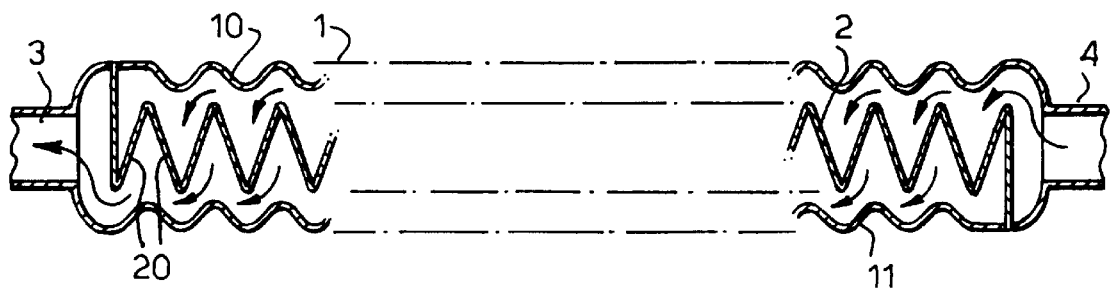
FIG. 2 is a simplified cross section side elevation view illustrating gas flow through the device.
Figure 3:
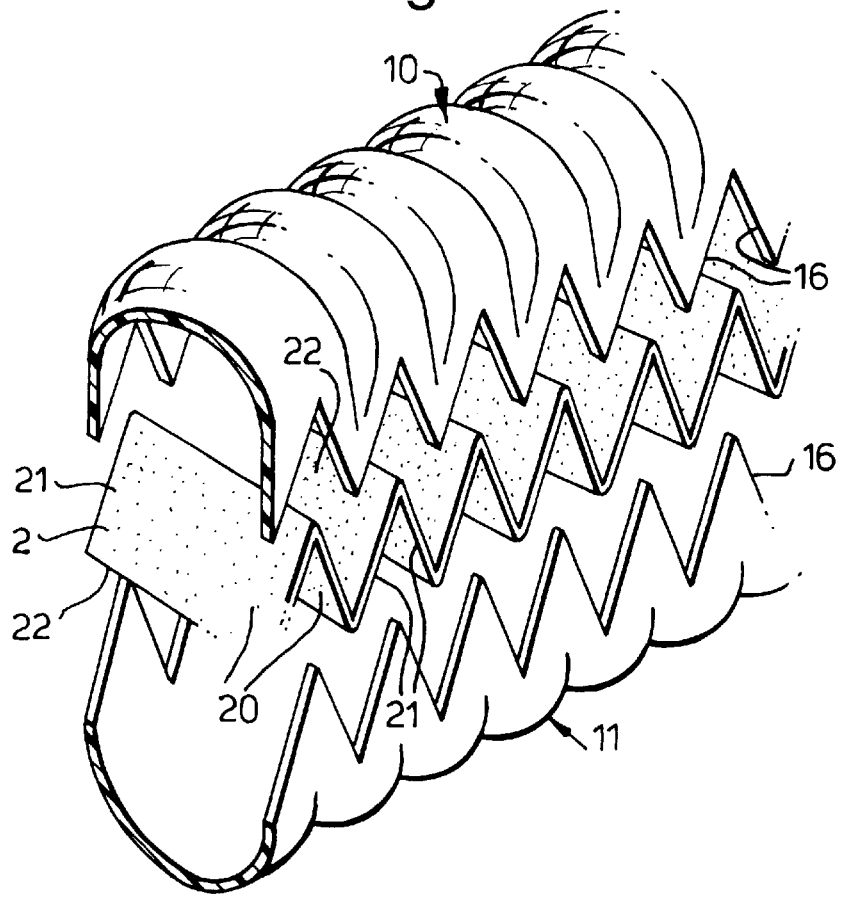
FIG. 3 is an exploded perspective view of a part of the device.
Figure 4:
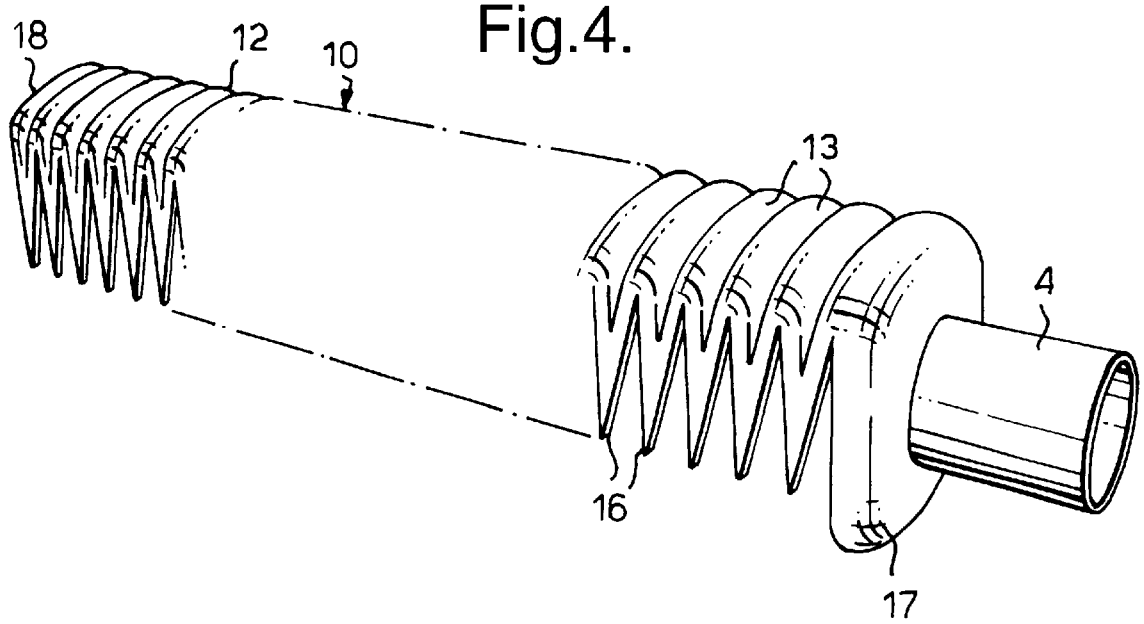
FIG. 4 is a perspective view of one part of the catheter mount housing.
Figure 6:
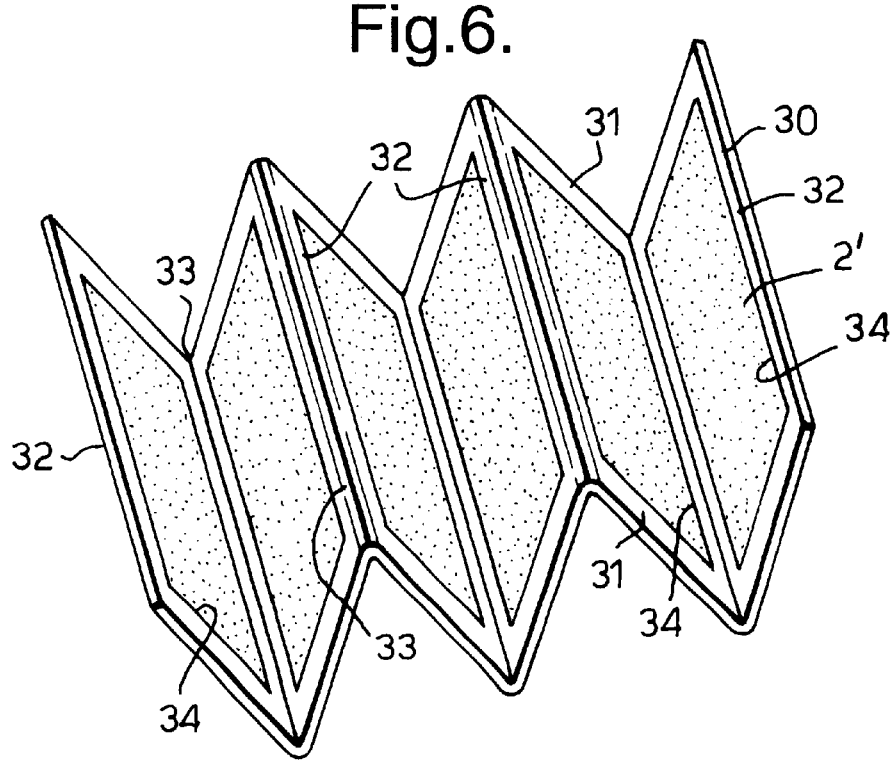
FIG. 6 is a perspective view of a part of a modified form of filter element.

If a delicate filter element is used, it may be necessary to protect it from damage caused by flexing of the element, either during use or during the pleating process. This may be done, in the manner shown in FIG. 6, by bonding the filter element 2' to a ladder-shape support frame 30, such as of an acetate material. The support frame 30 comprises two, narrow longitudinal strips 31 extending along the longitudinal edges of the filter element 2' and a number of lateral strips or rungs 32, one at each fold of the filter element. Each of the lateral strips 32 has a fold crease 33 to define the line of bend of the element. The space between adjacent lateral strips and longitudinal strips 32 and 31, forms a window 34 occupying most of the area of each pleat of the filter element. The longitudinal strips 31 of the support frame 30 are bonded between the teeth 16 of the two parts 10 and 11 of the housing 1, with the endmost lateral strips 32 being bonded between the flange 17 of one part and the end 18 of the other part. The support frame 30 is preferably of a thermoplastic material so that it can be bonded by heat both to the filter element and to the housing Flow of gas through the catheter mount is illustrated most clearly in FIG. 2. Gas entering the right-hand, machine port 4 flows along the lower part 11 of the housing 1, entering the upper part 10 only by flowing through the thickness of the filter element 2. Gas can flow in the same way through the catheter mount in the opposite direction. The catheter mount thereby serves a dual purpose of providing a flexible coupling between the tracheal tube and ventilation tubing, whilst also acting as a low resistance, high efficiency filter without any increase in the size of a conventional catheter mount. The invention also avoids the need for a separate component with the attendant disadvantages this brings, of increasing time and complexity of assembly, increasing deadspace, increased risk of accidental disconnection, increased risk of accidental omission of the filter and increased contaminated waste products for disposal after use.

The device of the present invention need not be a filter but could be some other form of fluid-treatment device, such as a heat and moisture exchanger employing a conventional HME element in place of the filter element. The device need not be used to treat gases but could be used to treat liquids.

What I claim is:

1. A fluid-treatment device, comprising:
   a flexible housing, the housing having an inlet port and an outlet port and being of elongate shape divided along a length of said housing into two parts defining a space internal to said two parts,
   wherein each part is corrugated transversely both internally and externally with respect to said space across a width of each part go that the housing is flexible transversely allowing the inlet port and the outlet port to be displaceably offset from each other transversely with respect to a longitudinal centerline of the housing when the housing is in an unflexed state,
   said two parts of said housing each having a set of triangular tooth formations extending along mating portions of said housing that mate with one another; and
   a fluid-treatment element within said space internal to said two parts, said fluid-treatment element being pleated across a width in a zigzag fashion with sides of said fluid-treatment element following a profile of said teeth formations on the housing, and with the pleats being substantially aligned with said corrugations and wherein opposite edges of said fluid-treatment element are supported and sealed between said teeth formation of the two parts of the housing such that fluid flowing between the inlet and outlet ports is confined to flow through the fluid-treatment element.

2. A fluid-treatment device according to claim 1, wherein the two parts of said housing are substantially identical.

3. A fluid-treatment device according to claim 1, wherein said fluid treatment element is a gas-treatment element.

4. A fluid-treatment device according to claim 3, wherein said fluid-treatment element is an HME element.

5. A fluid-treatment device according to claim 1, wherein said fluid-treatment element is a filter.

6. A fluid-treatment device according to claim 1, wherein one of said parts of the housing has a patient end fitting for connection to a tracheal tube connector.

7. A fluid-treatment device according to claim 6, wherein the other of said parts has a machine end fitting for connection to a ventilation tube connector.

8. A fluid-treatment device according to claim 1, wherein the said two parts of the housing are sealed with said fluid-treatment element by means of an adhesive or solvent along opposite edges of said fluid-treatment element.

9. A fluid-treatment device according to claim 1, wherein said device includes a ladder-shape support frame, and wherein said fluid-treatment element is supported by said frame.

10. A fluid-treatment device according to claim 9, wherein said support frame is of a thermoplastic material, and wherein the two said parts of the housing are sealed with said fluid-treatment element by flow of material of said support frame into sealing contact with both the fluid-treatment element and the said two parts of the housing.

11. A combined catheter mount and filter assembly for flexibly connecting a patient breathing device and ventilation tubing, the assembly comprising:
    a flexible, elongate housing defining a space,
    said housing being corrugated transversely both internally and externally with respect to said space across a width of the housing so that the housing is flexible transversely,
    the housing having an inlet port for connection to the ventilation tubing and an outlet port for connection to the patient breathing device; the housing being divided along a length of said housing into two parts,
    said housing having a flexibility such that said inlet port and said outlet port are transversely displaceable from each other with respect to a longitudinal centerline of said housing when said housing is in an unflexed state,
    wherein each of said two parts has a set of triangular tooth formations extending along mating sides of said housing that mate with one another; and a filter element within said space, said filter element being pleated across a width in a zigzag fashion with sides of said filter element following a profile of said tooth formations on the housing, and with the pleats being substantially aligned with said corrugations and wherein opposite edges of said filter element are supported and scaled between said teeth formation of the two parts of the housing such that fluid flowing between the inlet and outlet ports flows through the filter element.

12. A combined catheter mount and filter assembly for flexibly connecting a patient breathing device and ventilation tubing, the assembly comprising:

a flexible, elongate housing defining a space, said housing being corrugated transversely both internally and externally with respect to said space across a width of the housing so that the housing is flexible transversely, the housing having an inlet port for connection to the ventilation tubing and an outlet port for connection to the patient breathing device, the housing being divided along a length of said housing into two parts, said housing having a flexibility such that said inlet port and said outlet port are transversely displaceable from each other with respect to a longitudinal centerline of said housing when said housing is in an unflexed state, wherein each of said two parts has a set of triangular tooth formations extending along mating sides of said housing that mate with one another;

a filter element pleated across a width in a zigzag fashion with sides of said filter element following a profile of said tooth formations on the housing; and with the pleats being substantially aligned with said corrugations and a filter support frame of zig-zag shape having parallel, lateral strips extending across said filter in a region of pleats of said filter element and two longitudinal strips extending along opposite edges of said filter element, wherein said longitudinal strips are supported and sealed between said teeth formation of the two parts of the housing such that fluid flowing between the inlet and outlet ports flows through the filter element.

13. A combined catheter mount and HME assembly for flexibly connecting a patient breathing device and ventilation tubing, the assembly comprising:

a flexible, elongate housing defining a space, said housing being corrugated transversely both internally and externally with respect to said space across a width of the housing so that the housing is flexible transversely, the housing having an inlet port for connection to the ventilation tubing and an outlet port for connection to the patient breathing device, the housing being divided along a length of said housing into two parts, said housing having a flexibility such that said inlet port and said outlet port are transversely displaceable from each other with respect to a longitudinal centerline of said housing when said housing is in an unflexed state, wherein each of said two parts has a set of triangular tooth formations extending along mating sides of said housing that mate with one another;

an HME element within said space, said HME element being pleated across a width in a zigzag fashion with sides of said filter element following a profile of said tooth formations on the housing, and with the pleats being substantially aligned with said corrugations and wherein opposite edges of said HME element are supported and sealed between said tooth formation of the two parts of the housing such that fluid flowing between the inlet and outlet ports flows through the HME element.

14. A combined catheter mount and HME assembly for flexibly connecting a patient breathing device and ventilation tubing, the assembly comprising:

a flexible, elongate housing defining a space, said housing being corrugated transversely both internally and externally with respect to said space across a width of the housing so that the housing is flexible transversely, the housing having an inlet port for connection to the ventilation tubing and an outlet port for connection to the patient breathing device, the housing being divided along a length of said housing into two parts, said housing having a flexibility such that said inlet port and said outlet port are transversely displaceable from each other with respect to a longitudinal centerline of said housing when said housing is in an unflexed state, wherein each of said two parts has a set of triangular tooth formations extending along mating sides of said housing that mate with one another, and an HME element within said space, said HME element being pleated across a width in a zigzag fashion with sides of said filter element following a profile of said tooth formations on the housing; and with the pleats being substantially aligned with said corrugations and an HME support frame of zig-zag shape having parallel, lateral strips extending across said HME element in a region of pleats of said HME element and two longitudinal strips extending along opposite edges of said HME element, wherein said longitudinal skips are supported and sealed between said tooth formation of the two parts of the housing such that fluid flowing between the inlet and outlet ports flows through the HME element.

* * * * *